US012788246B2

(12) United States Patent
Nakamura et al.

(10) Patent No.: US 12,788,246 B2
(45) Date of Patent: Nov. 10, 2026

(54) OPHTHALMIC APPARATUS AND NON-TRANSITORY COMPUTER-READABLE STORAGE MEDIUM

(71) Applicant: NIDEK CO., LTD., Gamagori (JP)

(72) Inventors: Kenji Nakamura, Gamagori (JP); Toru Arikawa, Gamagori (JP); Yukihiro Higuchi, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 467 days.

(21) Appl. No.: 18/340,388

(22) Filed: Jun. 23, 2023

(65) Prior Publication Data

US 2023/0329551 A1 Oct. 19, 2023

Related U.S. Application Data

(63) Continuation of application No. PCT/JP2021/044669, filed on Dec. 6, 2021.

(30) Foreign Application Priority Data

Dec. 25, 2020 (JP) ................................ 2020-217515

(51) Int. Cl.
*A61B 3/15* (2006.01)
*A61B 3/00* (2006.01)

(52) U.S. Cl.
CPC ............ *A61B 3/152* (2013.01); *A61B 3/0041* (2013.01)

(58) Field of Classification Search
CPC ..... A61B 3/152; A61B 3/0041; A61B 3/0083; A61B 3/12; A61B 3/0075; A61B 3/102
See application file for complete search history.

(56) References Cited

U.S. PATENT DOCUMENTS 5,909,268 A 6/1999 Isogai et al.
5,909,269 A 6/1999 Isogai et al.
2016/0345822 A1* 12/2016 Fujimura .............. A61B 3/154

FOREIGN PATENT DOCUMENTS

EP 3 150 111 A1 4/2017
JP 10-127581 A 5/1998
(Continued)

OTHER PUBLICATIONS

International Search Report (PCT/ISA/210) issued by the International Searching Authority on Feb. 15, 2022 for International Patent Application No. PCT/JP2021/044669.
(Continued)

*Primary Examiner* — Sharrief I Broome
*Assistant Examiner* — K Muhammad
(74) *Attorney, Agent, or Firm* — Sughrue Mion, PLLC

(57) ABSTRACT

An ophthalmic apparatus includes an examination unit examining a subject eye, a drive unit moving the examination unit relative to the subject eye, a first imaging unit capturing a face image, a second imaging unit capturing an anterior segment image of the subject eye, a controller, and first and second acquisition units. The controller performs an adjustment process including a position acquisition of the subject eye based on the face image, a first drive control such that the subject eye is positioned within an imaging range of the second imaging unit based on the acquired position, and a second drive control based on the anterior segment image to adjust a position of the examination unit relative to the subject eye. The first acquisition unit acquires the position of the subject eye through a detection. The second acquisition unit acquires the position of the subject eye through an input operation.

5 Claims, 9 Drawing Sheets

(56) References Cited

FOREIGN PATENT DOCUMENTS

| | | | | | |
|---|---|---|---|---|---|
| JP | 10-216089 | A | | 8/1998 | |
| JP | 2006-288610 | A | | 10/2006 | |
| JP | 2009-15518 | A | | 1/2009 | |
| JP | 2014-205078 | A | | 10/2014 | |
| JP | 2015-64700 | A | | 4/2015 | |
| JP | 2017-64058 | A | | 4/2017 | |
| JP | 2017-80151 | A | | 5/2017 | |
| JP | 2017-196304 | A | | 11/2017 | |
| JP | 2019-63043 | A | | 4/2019 | |
| JP | 2020-156555 | A | | 10/2020 | |
| JP | 2021-40793 | A | | 3/2021 | |
| JP | 2021040793 | A | * | 3/2021 | |
| WO | WO-2017171058 | A1 | * | 10/2017 | ............... A61B 3/10 |

OTHER PUBLICATIONS

Written Opinion (PCT/ISA/237) issued by the International Searching Authority on Feb. 15, 2022 for International Patent Application No. PCT/JP2021/044669.

* cited by examiner

<SET DIRECTION IN WHICH EXAMINATION UNIT IS TO BE MOVED FROM INPUT>

SET DIRECTION IN WHICH EXAMINATION UNIT IS TO BE MOVED FROM INPUT

OPHTHALMIC APPARATUS AND NON-TRANSITORY COMPUTER-READABLE STORAGE MEDIUM

CROSS-REFERENCE TO RELATED APPLICATION(S)

This is a continuation application of International Application No. PCT/JP2021/044669 filed on Dec. 6, 2021 which claims priority from Japanese Patent Application No. 2020-217515 filed on Dec. 25, 2020. The entire contents of the earlier applications are incorporated herein by reference.

TECHNICAL FIELD

The present disclosure relates to an ophthalmic apparatus that examines a subject eye, and a non-transitory computer-readable storage medium storing a control program for the ophthalmic apparatus.

BACKGROUND

In an ophthalmic apparatus having an examination unit examining a subject eye, there is a technique for detecting positions of subject eyes by capturing a face image including left and right subject eyes and analyzing the captured face image. There is a technique in which after an examination unit is moved on the basis of detection results to perform rough alignment of the examination unit with respect to a subject eye, automatic alignment is performed to transition to fine alignment based on an anterior segment image obtained by imaging the anterior segment (refer to, for example, JP2017-064058A).

However, when a face image is analyzed to detect a position of a subject eye, depending on the condition of a subject's face or an examination environment, the position of the subject eye may not be detected, the position of the subject eye may be erroneously detected, or it may take a long time to detect the subject eye. In such a case, there is a problem that alignment is not favorably performed.

SUMMARY

An object of the present disclosure is to provide an ophthalmic apparatus and a non-transitory computer-readable storage medium storing a control program for the ophthalmic apparatus which can perform favorable alignment.

(1) An ophthalmic apparatus includes an examination unit configured to examine a subject eye, a drive unit configured to three-dimensionally move the examination unit relative to the subject eye, a first imaging unit configured to capture a face image including left and right subject eyes, a second imaging unit configured to capture an anterior segment image of the subject eye, a controller configured to perform an adjustment process including a position acquisition of acquiring a position of the subject eye which is identified based on the face image, a first drive control of controlling the drive unit, such that the subject eye is positioned within an imaging range of the second imaging unit, based on the acquired position of the subject eye, and a second drive control of controlling the drive unit based on the anterior segment image after the first drive control, to adjust a relative position of the examination unit with respect to the subject eye, a first acquisition unit configured to detect a position of the subject eye by analyzing the face image, and acquire the position of the subject eye identified through the detection as a detected position; and a second acquisition unit configured to receive an input operation for designating a position of the subject eye in the face image, and acquire the position of the subject eye identified based on the input operation as a designated position.

(2) A non-transitory computer-readable storage medium storing a control program for an ophthalmic apparatus including a drive unit configured to three-dimensionally move an examination unit, which examines a subject eye, relative to the subject eye, a first imaging unit configured to capture a face image including left and right subject eyes, and a second imaging unit configured to capture an anterior segment image of the subject eye, the control program including instructions which, when executed by a controller of the ophthalmic apparatus, cause the ophthalmic apparatus to perform a control step of performing an adjustment process including a position acquisition of acquiring a position of the subject eye which is identified based on the face image, a first drive control of controlling the drive unit, such that the subject eye is positioned within an imaging range of the second imaging unit, based on the acquired position of the subject eye, and a second drive control of controlling the drive unit based on the anterior segment image after the first drive control, to adjust a relative position of the examination unit with respect to the subject eye, a first acquisition step of detecting a position of the subject eye by analyzing the face image and acquiring the position of the subject eye identified through the detection as a detected position, and a second acquisition step of receiving an input operation for designating a position of the subject eye in the face image, and acquiring the position of the subject eye identified based on the input operation as a designated position.

DETAILED DESCRIPTION

Figure 1:
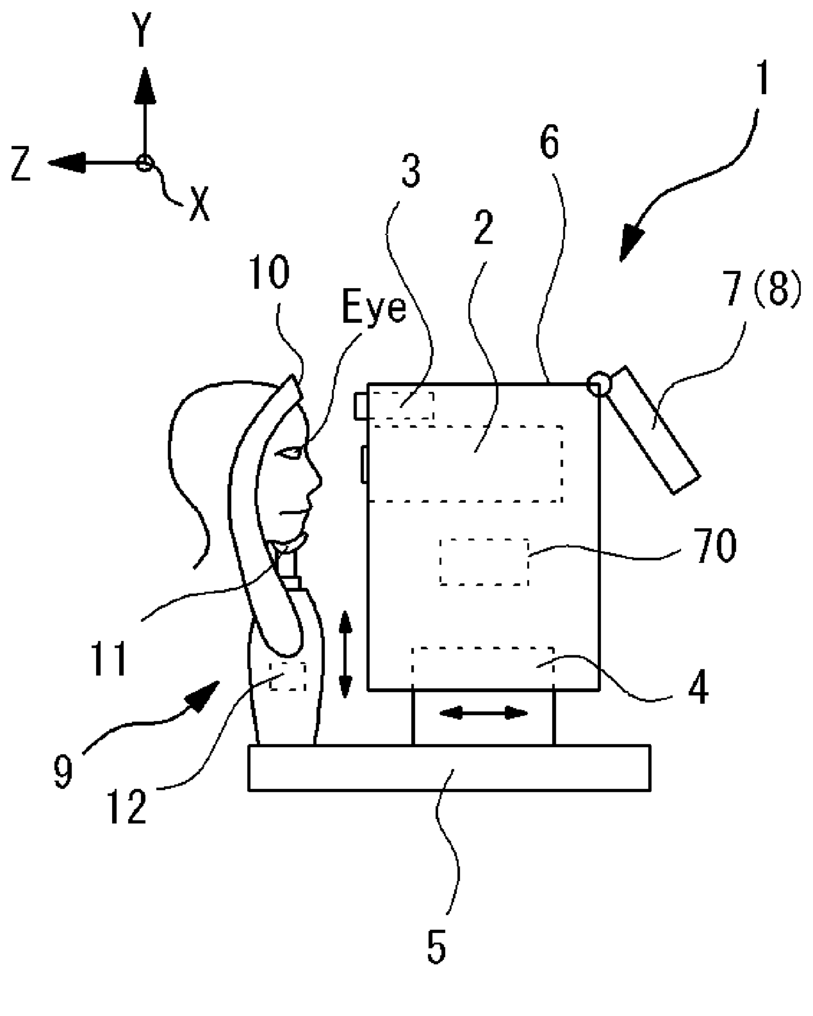
FIG. 1 is a schematic external view of an ophthalmic apparatus.

Hereinafter, embodiments of the present disclosure will be described below with reference to the drawings. FIGS. 1 to 12 are diagrams for describing a configuration of an ophthalmic apparatus according to an embodiment.

Outline

For example, an ophthalmic apparatus (for example, an ophthalmic apparatus 1) includes an examination unit (for example, an examination unit 2) for examining a subject eye, a drive unit (for example, a drive unit 4), a first imaging unit (for example, a face imaging unit 3), a second imaging unit (for example, an anterior segment imaging optical system 60), a controller (for example, the control unit 70), a first acquisition unit (for example, a control unit 70), and a second acquisition unit (for example, a control unit 70).

For example, the examination unit includes an examination optical system (for example, a measurement optical system 20) for examining (including measuring) a subject eye.

For example, the ophthalmic apparatus may include at least any of a base (for example, a base 5) on which the examination unit is mounted, a face support unit (for example, a face support unit 9), a detection unit (for example, a control unit 70), an input unit (for example, an operation unit 8), a notification unit (for example, a display 7), a display unit (for example, a display 7), and a determination unit (for example, a control unit 70).

For example, the face support unit is configured to support a subject's face in a fixed positional relationship with respect to the base. For example, the face support unit may include a jaw rest on which a subject's jaw rests.

For example, the drive unit is configured to three-dimensionally move the examination unit relative to a subject eye. For example, the examination unit is mounted on the base to be movable in an X direction (horizontal direction), a Y direction (vertical direction), and a Z direction (front-rear direction) with respect to the subject eye of the subject supported by the face support unit. For example, the drive unit moves the examination unit in the X direction, Y direction and Z direction with respect to the base. For example, the ophthalmic apparatus may include a jaw rest drive unit (for example, a jaw rest drive unit 12). For example, the jaw rest drive unit is provided on the face support unit to drive the jaw rest in the Y direction. In this case, the drive unit may include the jaw rest drive unit as a configuration for moving the examination unit relative to the subject eye in the Y direction.

For example, the first imaging unit is configured to capture a face image including left and right subject eyes.

For example, the second imaging unit is configured to capture an anterior segment image of the subject eye. For example, the second imaging unit is configured to capture the anterior segment image of the subject eye at an imaging magnification higher than that of the first imaging unit. For example, the first imaging unit may also be used as the second imaging unit, and may be configured such that the imaging magnification can be changed.

For example, the detection unit precisely detects an alignment state of the examination unit with respect to the subject eye that is an examination target on the basis of the anterior segment image obtained by the second imaging unit.

For example, the display unit displays the face image captured by the first imaging unit. For example, the display unit may display the anterior segment image captured by the second imaging unit. For example, the display unit may simultaneously display the face image and the anterior segment image. In this case, for example, the controller may control to display the face image to be larger than the anterior segment image when performing alignment based on the face image. The controller may control to display the anterior segment image to be larger than the face image when transitioning to the alignment based on the anterior segment image. For example, a positional relationship between the subject eye and the examination unit is adjusted through alignment based on the face image until alignment based on the anterior segment image becomes possible. For example, a positional relationship between the subject eye and the examination unit is aligned with a predetermined positional relationship through alignment based on the anterior segment image. The predetermined positional relationship is, for example, a positional relationship between the subject eye and the examination unit at which examination can be performed by the examination unit.

For example, the input unit is provided in the ophthalmic apparatus for the examiner to designate and input the position corresponding to the subject eye with respect to the face image captured by the first imaging unit. For example, the input unit is capable of inputting a designated position for roughly aligning the examination unit with respect to the subject eye. For example, the input unit includes a pointing device (for example, at least one of human interfaces such as a touch panel, a joystick, a mouse, a keyboard, a trackball, and buttons). For example, the input unit can input a designated position for the face image displayed on the display unit during rough alignment. For example, the face image for which the designated position is input may be a moving image captured by the first imaging unit, or may be a still image.

For example, the controller performs an adjustment process of adjusting a relative position of the examination unit with respect to the subject eye by controlling the drive unit. For example, the adjustment process performed by the controller includes a position acquisition, a first drive control, and a second drive control.

For example, the position acquisition is a process of acquiring a position of the subject eye identified on the basis of the face image.

For example, the first drive control is a process of controlling the drive unit, such that the subject eye is positioned within an imaging range of the second imaging unit. For example, the first drive control may be rough alignment for roughly aligning the examination unit with respect to the subject eye.

For example, the second drive control is a process of controlling the drive unit on the basis of the anterior segment image after the first drive control, and adjusting a relative position of the examination unit with respect to the subject eye. For example, the second drive control may be fine alignment for precisely aligning the examination unit with respect to the subject eye.

For example, the first acquisition unit detects a position of the subject eye by analyzing the face image, and acquires the position of the subject eye identified as a result of detection as a detected position.

For example, the second acquisition unit receives an input operation for the position of the subject eye on the face image, and acquires the position of the subject eye identified on the basis of the input operation as the designated position. For example, in the position acquisition, the second acquisition unit may acquire a designated position on the basis of an input operation for an eye position on the face image displayed on the display unit. For example, the controller performs the adjustment process of the first drive control on the basis of the position of the subject eye acquired by the second acquisition unit.

For example, the second acquisition unit detects a position of the subject eye by using a part of the face image as an analysis target based on coordinates designated through an input operation on the face image, and acquires the position of the subject eye identified as a result of the detection as a designated position. For example, the part of the face image that is an analysis target is within a predetermined region based on designated coordinates.

For example, in the position acquisition, in a case where there are a plurality of candidates of a position of the subject eye that are identified on the basis of the face image, the display unit may display the identified candidates of the position of the subject eye. In this case, the second acquisition unit acquires a candidate designated from among the plurality of candidates according to input operation of the examiner as a designated position.

For example, since the second acquisition unit is provided, alignment can be favorably performed in a case where a position of the subject eye cannot be detected by the first acquisition unit due to the condition of the subject's face (for example, the subject's mascara, eyelashes, or ptosis) or an examination environment (the background of the subject's face imaged by the first imaging unit, illumination light, ambient light, and the like) or in a case where it takes a long time to detect the subject eye.

For example, in a case where an input operation for a designated position is received after the adjustment process using the detected position is started, the controller may perform the first drive control on the basis of the designated position regardless of a position detected by the first acquisition unit. Accordingly, alignment can be favorably performed even in a case where it takes a long time to detect the subject eye in the first acquisition unit.

For example, in a case where the left eye and the right eye are examined consecutively, the controller may collectively acquire respective positions of the left eye and the right eye in the position acquisition in a process of adjusting one subject eye examined first out of the left eye and the right eye. In the position acquisition, in a case where the respective positions of the left eye and the right eye are collectively acquired, an input operation for each subject eye may be requested. As a result, the examiner can understand that it is necessary to input the positions of the left eye and the right eye, and can prevent forgetting to input the positions.

In a case where the left eye and the right eye are examined consecutively, the controller may perform the first drive control in a predetermined procedure by using a designated position corresponding to one subject eye, and perform the first drive control by using a designated position corresponding to the other eye after the examination for the one eye is completed. In this case, for example, the ophthalmic apparatus may be provided with the determination unit (for example, the control unit 70) for determining whether one of the two designated positions corresponds to the left eye or the right eye.

For example, the determination unit determines whether one of the two designated positions corresponds to the left eye or the right eye on the basis of a positional relationship between the two designated positions or a positional relationship between the designated positions on the face image. For example, the controller determines, out of the two designated positions, a designated position corresponding to one subject eye set in advance to be examined first, on the basis of determination results of the left eye and the right eye, and starts to execute the first drive control. As a result, favorable alignment can be performed in both-eye examination.

The predetermined procedure is, for example, a procedure of determining which of the left and right subject eyes is to be examined first. The predetermined procedure may be defined, for example, to start the examination from a subject eye of which a designated position is input first.

For example, the controller may wait to perform the first drive control until two positions of the left eye and right eye are input. For example, after a position of one of the left and right eyes is input, in a case where a position of the other eye is not input within a predetermined period of time, the notification unit notifies an examiner to prompt an input operation for the position of the subject eye (for example, the display 7) may be provided in the ophthalmic apparatus. Alternatively, for example, in a case where the position of the other eye is not input within a predetermined period of time, the controller may start to perform the first drive control using the position of one eye.

For example, in a case where a single designated position is input through an input operation, the determination unit may be configured to determine the left and right subject eyes on the basis of whether the designated position is present in the right eye region or the left eye region in the face image. In this case, for example, the controller performs the first drive control on the basis of the input designated position, then shirts to the second drive control, and after the examination of one of the left and right subject eyes is completed, determines a left or right direction in which the examination unit is moved relative to the subject eye on the basis of the determination result from the determination unit in order to examine the unexamined subject eye, controls the drive unit such that the examination unit comes close to the unexamined subject eye on the basis of the determined direction, and shirts to the second drive control. As a result, even in a case where there is only one designated position, alignment can be favorably performed in consecutive examination of both the left and right eyes.

For example, in the adjustment process using a detected position, the notification unit performs, in a case where acquisition of the detected position fails (that is, in a case where an acquisition error occurs), a notification for requesting the examiner to perform the input operation for the designated position. Consequently, the examiner can ascertain that the detection of the position of the subject eye in the first acquisition unit is defective, and can favorably perform alignment by performing an input operation for a position of the subject eye.

The present disclosure is not limited to the apparatus described in the present embodiment. For example, a control program (software) for performing the functions of the above-described embodiment may be supplied to a system or an apparatus via a network or various storage media. A control unit (for example, a CPU or the like) of the system or the apparatus can read and execute the program.

For example, the control program executed in the ophthalmic apparatus may cause the ophthalmic apparatus to perform a control step of performing an adjustment process of adjusting a relative position of the examination unit with respect to the subject eye by being executed by the control unit of the ophthalmic apparatus. For example, the control step includes various processing steps as described above performed by the controller.

EXAMPLE

An ophthalmic apparatus according to the present disclosure will be described with reference to the drawings. In the following description, an eye refractive power measurement apparatus will be described as an example of an ophthalmic apparatus, but the present disclosure is also applicable to other ophthalmic apparatuses such as a corneal curvature measurement apparatus, an intraocular pressure measurement apparatus, a fundus camera, an optical coherence tomography (OCT), a scanning laser ophthalmoscope (SLO), and a micro perimeter.

The ophthalmic apparatus of the present example objectively measures, for example, an eye refractive power of a subject eye. For example, the ophthalmic apparatus of the present example may be an apparatus that performs measurement for each eye, or performs measurement for both eyes simultaneously (with both-eye vision). The ophthalmic apparatus mainly includes, for example, an examination unit, an imaging unit, a drive unit, and a control unit.

With reference to FIG. 1, an exterior of the ophthalmic apparatus will be described. As illustrated in FIG. 1, an ophthalmic apparatus 1 of the present example mainly includes an examination unit 2, a face imaging unit 3 and a drive unit 4. The examination unit 2 examines a subject eye. The examination unit 2 may include, for example, an optical system that measures an eye refractive power, a corneal curvature, an intraocular pressure, or the like of the subject eye. The examination unit 2 may include an optical system or the like that images an anterior segment, the fundus, or the like of the subject eye. In the present example, the examination unit 2 that measures a refractive power will be described as an example. The face imaging unit 3 captures, for example, a subject's face. The face imaging unit 3 captures, for example, a face including left and right subject eyes. The drive unit 4 moves, for example, the examination unit 2 and the face imaging unit 3 with respect to the base 5 in vertical, horizontal, and front-rear directions (three-dimensional directions).

The ophthalmic apparatus 1 of the present example may include, for example, a casing 6, a display 7, an operation unit 8, a face support unit 9, and the like. For example, the casing 6 accommodates the examination unit 2, the face imaging unit 3, the drive unit 4, and the like.

The display 7 displays, for example, a face image If captured by the face imaging unit 3, an anterior segment image Ia captured by and measurement results from the anterior segment imaging optical system 60, and the like. For example, display on the display 7 is switched from the face image If to the anterior segment image Ia when fine alignment (refer to FIG. 4) that will be described later is started. For example, the display 7 may simultaneously display the face image If and the anterior segment image Ia. For example, the control unit 70 may display the face image If or the anterior segment image Ia selected by the examiner on the display 7. In that case, for example, the ophthalmic apparatus 1 is provided with a selection unit (for example, a switch) for selecting whether to display either the face image If or the anterior segment image Ia. The display 7 may be provided integrally with, for example, the ophthalmic apparatus 1 or may be provided separately from the apparatus.

For example, the ophthalmic apparatus 1 may include an operation unit 8. For example, the operation unit 8 has a pointing device that can designate a position on a screen of the display 7. The pointing device may be any of various human interfaces such as touch panels, joysticks, mice, keyboards, trackballs, and buttons. Various operation instructions are input to the operation unit 8 by the examiner.

In the present example, the display 7 has a touch function, and the operation unit 8 is also used as the display 7. That is, the ophthalmic apparatus 1 is operated by the examiner touching the display 7. The operation unit 8 is used for various settings of the ophthalmic apparatus 1 and operations at the start of measurement. In the present example, the operation unit 8 is used for the examiner to designate coordinates (position) on the face image If displayed on the display 7. For example, two-dimensional coordinate axes (x-axis and y-axis) are set in advance on the display 7 by a program, and a position (designated point) touched by the examiner is recognized by the control unit 70 (refer to FIG. 2). The two-dimensional coordinate axes (x-axis and y-axis) on the display 7 are names given for description, and are different from the X direction (horizontal direction), the Y direction (vertical direction), and the Z direction (front-rear direction) in which the examination unit 2 is driven.

The configuration of the control unit 70 recognizing touch input is the same as that disclosed in JP2014-205078A, which is desired to be referred to.

The face support unit 9 may include, for example, a forehead rest 10 and a jaw rest 11. The jaw rest 11 may be vertically moved as a result of driving of the jaw rest drive unit 12.

Figure 2:
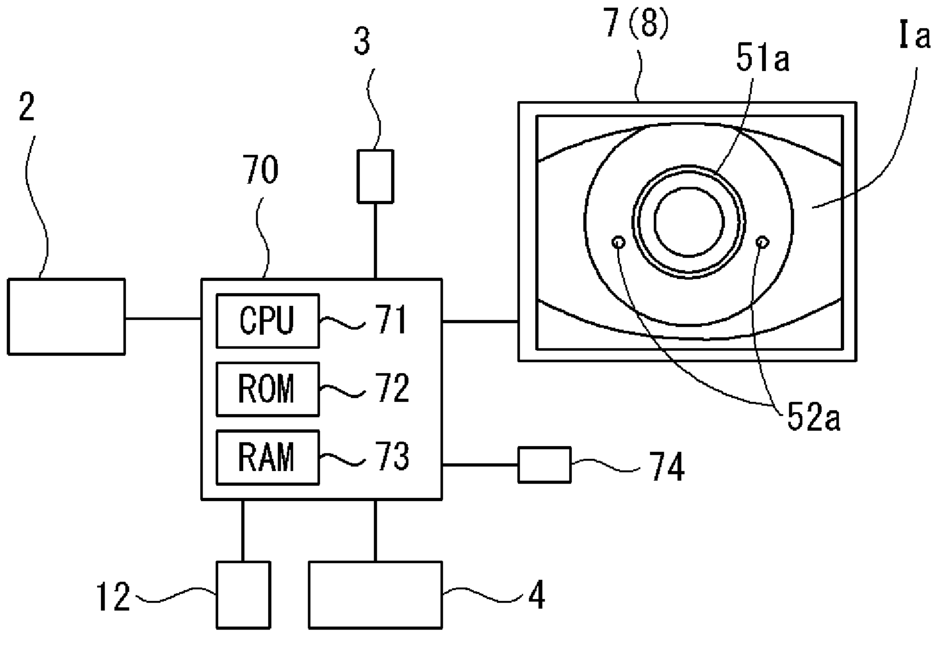
FIG. 2 is a block diagram illustrating a control system of the ophthalmic apparatus.

As illustrated in FIG. 2, the ophthalmic apparatus 1 includes a control unit 70. The control unit 70 performs various types of control of the ophthalmic apparatus 1. For example, the control unit 70 includes a general central processing unit (CPU) 71, a flash ROM 72, a RAM 73, and the like. For example, the flash ROM 72 stores a control program for controlling the ophthalmic apparatus 1, initial values, and the like. For example, the RAM temporarily stores various types of information. The control unit 70 is connected to the examination unit 2, the face imaging unit 3, the drive unit 4, the display 7, the operation unit 8, the jaw rest drive unit 12, the storage unit (for example, a non-volatile memory) 74, and the like. For example, the storage unit 74 is a non-transitory storage medium that can retain stored content even when the power supply is interrupted. For example, a hard disk drive, a flash ROM, or a detachable USB memory may be used as the storage unit 74.

Figure 3:
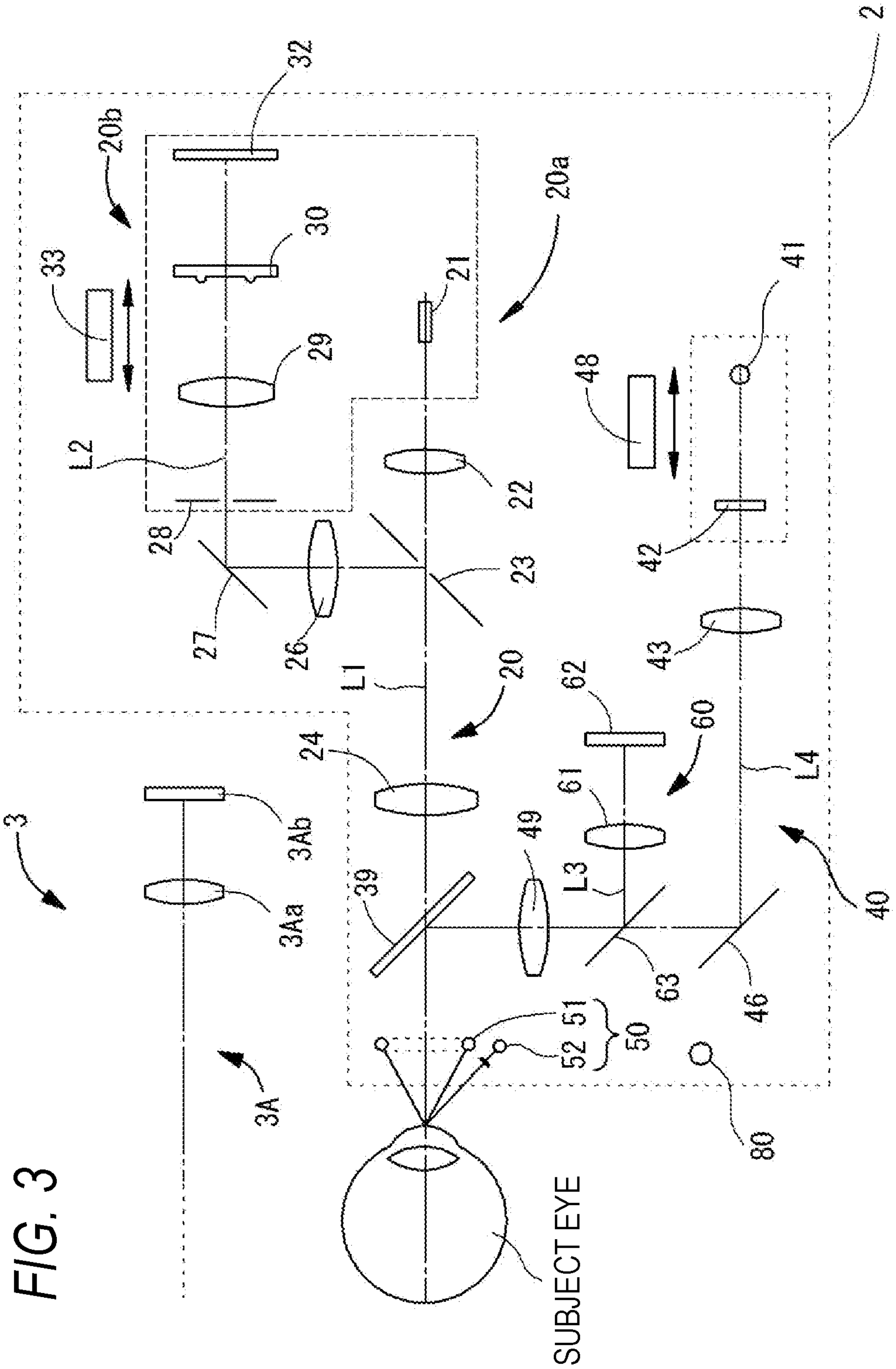
FIG. 3 is a schematic diagram illustrating an optical system of the ophthalmic apparatus.

The face imaging unit 3 can photograph, for example, a face including left and right subject eyes. For example, as illustrated in FIG. 3, the face imaging unit 3 of the present example includes an imaging optical system 3A that photographs a subject's face. The imaging optical system 3A mainly includes, for example, an imaging element 3Aa and an imaging lens 3Ab. The face imaging unit 3 is, for example, a non-telecentric optical system. This eliminates the need for a telecentric lens, or the like and simplifies the configuration. An imaging range can be widened compared with that of a telecentric optical system.

The face imaging unit 3 of the present example is moved together with the examination unit 2 by the drive unit 4. Of course, the face imaging unit 3 may be configured to be fixed to the base 5 and prevented from being moved.

In the present example illustrated in FIG. 1, the face imaging unit 3 is provided above the examination unit 2, but a position of the face imaging unit 3 is not limited to this. For example, the face imaging unit 3 may be provided below the examination unit 2 or may be provided on the side thereof. In the present example, the position of the face imaging unit 3 (the optical axis of the imaging optical system 3A) in the horizontal direction is the same position as an optical axis L2 of the examination unit 2, but is not limited to this. For example, assuming that measurement is started from the right eye of the subject, the face imaging unit 3 may be located at the center of the base 5 in the horizontal direction similarly to the jaw rest 11 in a state in which an initial position of the examination unit 2 in the horizontal direction is located on the right eye side as seen from the subject. Of course, the face imaging unit 3 may be provided such that a measurement optical axis of the examination unit 2 and an imaging optical axis of the face imaging unit 3 are coaxial. The face imaging unit 3 may be disposed independently of the movement of the examination unit 2. For example, the face imaging unit 3 is provided on the base 5 to be capable of being driven three-dimensionally, and may be driven three-dimensionally with respect to the subject eye by a drive unit (second drive unit) different from the drive unit (first drive unit) 4. Of course, the first drive unit that moves the examination unit 2 and the second drive unit that moves the face imaging unit 3 may be used in common as in the present example.

The examination unit 2 performs a measurement, an examination, an imaging, and the like of a subject eye. The examination unit 2 may include, for example, a measurement optical system that measures a refractive power of the subject eye. For example, as illustrated in FIG. 3, the examination unit 2 may include a measurement optical system 20, a fixation target presentation optical system 40, an alignment mark projection optical system 50, and an observation optical system (anterior segment imaging optical system) 60.

The measurement optical system 20 has a projection optical system (light projecting optical system) 20*a* and a light receiving optical system 20*b*. The projection optical system 20*a* projects a luminous flux onto the fundus Ef via the pupil of the subject eye. The light receiving optical system 20*b* extracts a ring-shaped reflected luminous flux (fundus reflected light) from the fundus Ef via the peripheral portion of the pupil, and photographs a ring-shaped fundus reflected image mainly used for refractive power measurement.

The projection optical system 20*a* has a light source 21, a relay lens 22, a hole mirror 23, and an objective lens 24 on the optical axis L1. The light source 21 projects a spot-like light source image onto the fundus Ef via the relay lens 22, the objective lens 24, and the center of the pupil. The light source 21 is moved in the direction of the optical axis L1 by a movement mechanism 33. The hole mirror 23 is provided with an opening through which the luminous flux from the light source 21 via the relay lens 22 passes. The hole mirror 23 is disposed at a position optically conjugate to the pupil of the subject eye.

The light receiving optical system 20*b* shares the hole mirror 23 and the objective lens 24 with the projection optical system 20*a*. The light receiving optical system 20*b* also has a relay lens 26 and a total reflection mirror 27. The light receiving optical system 20*b* has a light receiving diaphragm 28, a collimator lens 29, a ring lens 30, and an imaging element 32 on the optical axis L2 in the reflection direction of the hole mirror 23. A two-dimensional light receiving element such as an area CCD may be used for the imaging element 32. The light receiving diaphragm 28, the collimator lens 29, the ring lens 30, and the imaging element 32 are moved in the direction of the optical axis L2 together with the light source 21 of the projection optical system 20*a* by the movement mechanism 33. In a case where the light source 21 is disposed at a position optically conjugate to the fundus Ef by the movement mechanism 33, the light receiving diaphragm 28 and the imaging element 32 are also disposed at a position optically conjugate to the fundus Ef.

The ring lens 30 is an optical element for shaping the fundus reflected light guided from the objective lens 24 via the collimator lens 29 into a ring shape. The ring lens 30 has a ring-shaped lens portion and a light blocking portion. In a case where the light receiving diaphragm 28 and the imaging element 32 are disposed at the position optically conjugate to the fundus Ef, the ring lens 30 is disposed at a position optically conjugate to the pupil of the subject eye. The imaging element 32 receives the ring-shaped fundus reflected light (hereinafter referred to as a ring image) via the ring lens 30. The imaging element 32 outputs image information of the received ring image to the control unit 70. As a result, the control unit 70 displays the ring image on the display 7 and calculates a refractive power or the like based on the ring image.

As illustrated in FIG. 3, in the present example, a dichroic mirror 39 is disposed between the objective lens 24 and the subject eye. The dichroic mirror 39 transmits light emitted from the light source 21 and fundus reflected light corresponding to the light from the light source 21 therethrough. The dichroic mirror 39 guides a luminous flux from the fixation target presentation optical system 40 that will be described later to the subject eye. The dichroic mirror 39 reflects anterior segment reflected light of the light from the alignment mark projection optical system 50 that will be described later and guides the anterior segment reflected light to the anterior segment imaging optical system 60.

As illustrated in FIG. 3, the alignment mark projection optical system 50 is disposed in front of the subject eye. The alignment mark projection optical system 50 mainly projects a mark image used for alignment of the optical system with the subject eye onto the anterior segment. The alignment mark projection optical system 50 includes a ring mark projection optical system 51 and a mark projection optical system 52. The ring mark projection optical system 51 projects diffused light onto the cornea of the subject eye E to project a ring mark 51*a*. The ring mark projection optical system 51 is also used as an anterior segment light that illuminates the anterior segment of the subject eye E in the ophthalmic apparatus 1 of the present example. The mark projection optical system 52 projects parallel light onto the cornea of the subject eye to project an infinity mark 52*a*.

The fixation target presentation optical system 40 has a light source 41, a fixation target 42, and a relay lens 43 on an optical axis L4 in a reflection direction of a reflection mirror 46. The fixation target 42 is used to fixate the subject eye during objective refractive power measurement. For example, the light source 41 illuminates the fixation target 42 to be presented to the subject eye.

The light source 41 and the fixation target 42 are integrally moved in the direction of the optical axis L4 by the drive mechanism 48. A presentation position (presentation distance) of the fixation target may be changed by moving the light source 41 and the fixation target 42. As a result, the refractive power can be measured by applying fog to the subject eye.

The anterior segment imaging optical system 60 includes an imaging lens 61 and an imaging element 62 on an optical axis L3 in a reflection direction of a half mirror 63. The imaging element 62 is disposed at a position optically conjugate to the anterior segment of the subject eye. The imaging element 62 photographs the anterior segment illuminated by the ring mark projection optical system 51. An output from the imaging element 62 is input to the control unit 70. As a result, the anterior segment image Ia of the subject eye captured by the imaging element 62 is displayed on the display 7 (refer to FIG. 2). The imaging element 62 captures an alignment mark image (the ring mark 51*a* and the infinity mark in the present example) formed on the cornea of the subject eye by the alignment mark projection optical system 50. As a result, the control unit 70 can detect the alignment mark image on the basis of the imaging result from the imaging element 62. The control unit 70 can determine whether or not an alignment state is appropriate on the basis of a position at which the alignment mark image is detected.

<Both-Eye Examination>

Figure 4:
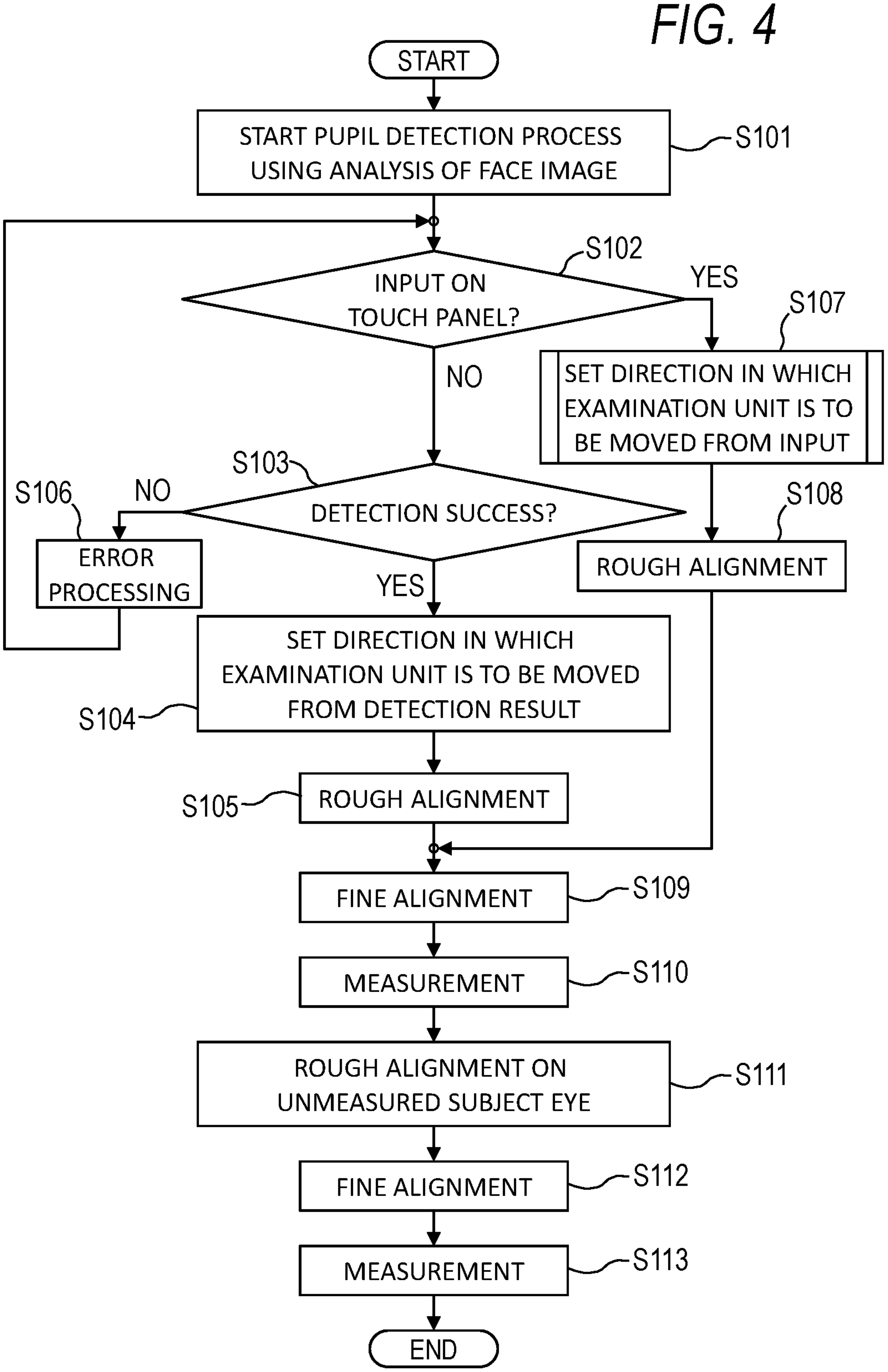
FIG. 4 is a flowchart illustrating an operation of the ophthalmic apparatus.
Figure 5:
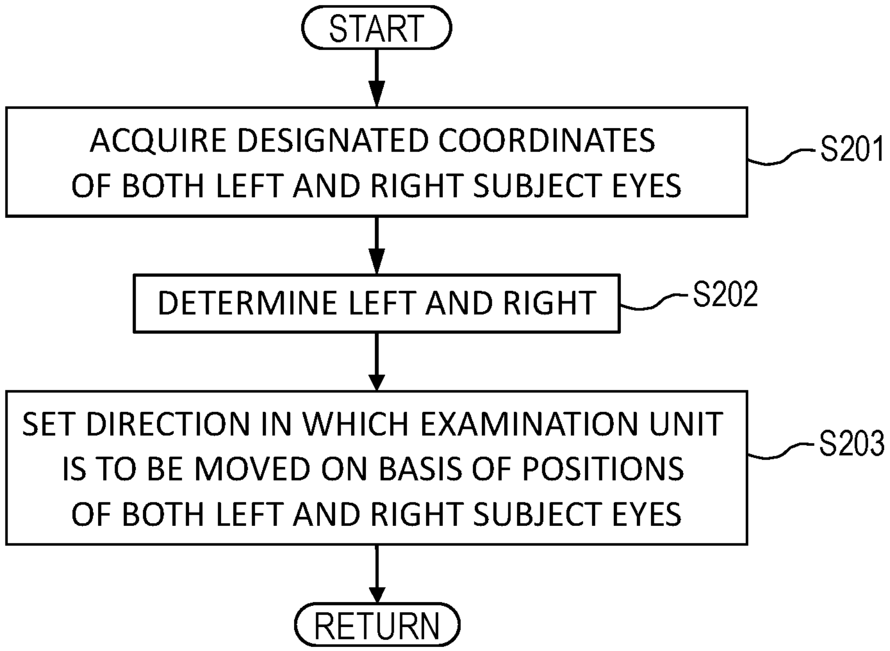
FIG. 5 is a flowchart illustrating an operation of the ophthalmic apparatus in a case where positions of left and right subject eyes are input.

Hereinafter, an operation of the ophthalmic apparatus 1 of the present example will be described with reference to flowcharts of FIGS. 4 and 5. In the present example, for example, detection of a position of the pupil of the subject eye based on the face image If, rough alignment that is alignment based on the detected position of the pupil, and fine alignment that is alignment based on the anterior segment image Ia are automatically performed. The control unit 70 performs measurement (examination) when the fine alignment is completed. The flowcharts of FIGS. 4 and 5 illustrate a case where the right eye and the left eye of the subject are examined consecutively.

In the present example, a position of the pupil is detected as a position of the subject eye, but the content of the present disclosure is not limited to this, and other characteristic parts such as the inner corner of the eye may be detected.

(1) In Case where Position of Subject Eye is Normally Detected Through Analysis of Face Image First, a case where a position of a subject eye is normally detected by analyzing a face image captured by the face imaging unit 3 will be described.

Figure 7:
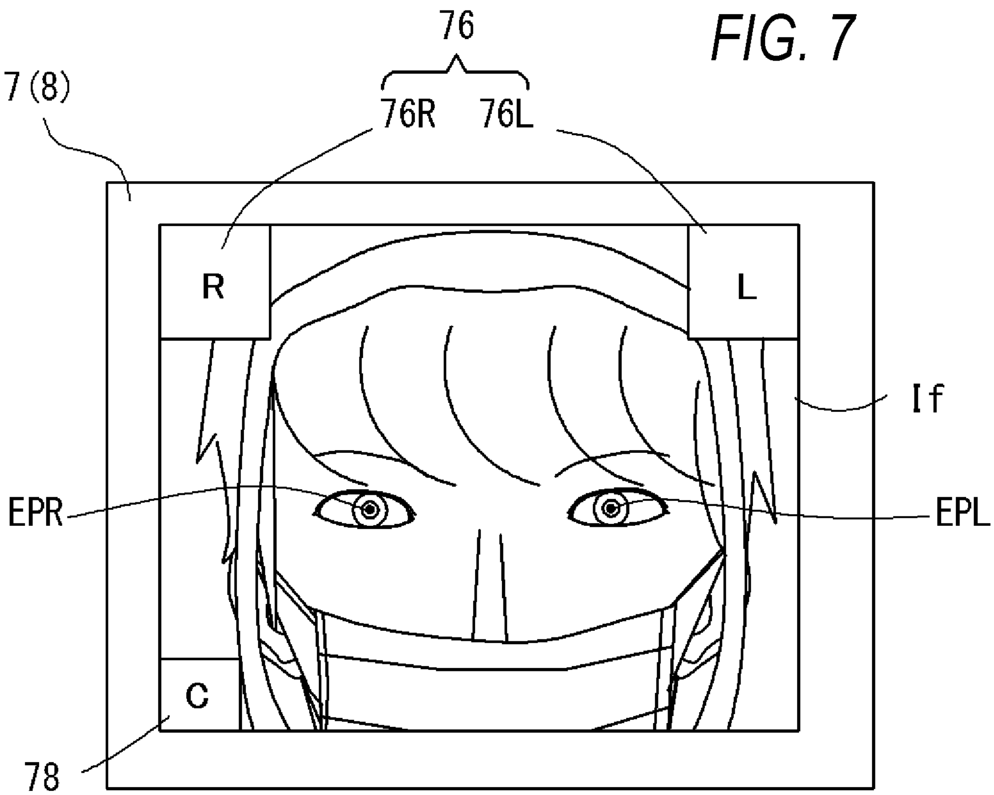
FIG. 7 is a schematic diagram of a display in a case where a position of a subject eye is detected through analysis of the face image.

For example, in an initial state before the start of the examination, the examination unit 2 is located at the center in the horizontal direction with respect to the base 5 in the rear position away from the subject. In this state, as illustrated in FIG. 7, the face image If including the left and right subject eyes of the subject is imaged by the face imaging unit 3, and the control unit 70 acquires the face image If. The control unit 70 analyzes the acquired face image If and detects positions of the left and right pupils (right eye pupil EPR and left eye pupil EPL) (S101). The pupil position of the subject eye identified through the detection is acquired as a detected position. For example, the control unit 70 may detect an edge of the face image and detect a position of the pupil from the face image on the basis of a shape of the edge. As an example of a pupil detection method, refer to the method disclosed in JP2017-196304A.

Thereafter, in a case where there is no input on the display 7 (touch panel) (S102: No) and the control unit 70 determines that the pupil positions of both eyes have been detected on the basis of the face image (S103: Yes), a direction in which the examination unit is to be moved on the basis of the detected left and right pupil positions is set (S104), and rough alignment is performed (S105).

A method of setting a direction in which the control unit 70 will move the examination unit 2 in S104 will be briefly described. Regarding the left and right subject eyes, a subject eye to be examined first is programmed in advance. For example, it is preset to start examination from the right eye.

The control unit 70 identifies the right eye pupil EPR out of the pupil positions of both eyes detected through the analysis of the face image If. The control unit 70 performs calculation on the basis of the identified position (x, y) (two-dimensional coordinates) of the right eye pupil EPR, and obtains the examination unit 2 of the direction in which the right eye pupil EPR is present (three-dimensional coordinates). Thereafter, the control unit 70 controls driving of the drive unit 4 to move the examination unit 2 in the obtained direction, and thus performs rough alignment on the right eye (S105).

A method of determining a direction in which the subject eye is present from the coordinates on the face image If (that is, a rough alignment method) may employ the technique disclosed in the publications (for example, refer to JP2017-064058A and JP2019-063043A).

Next, the control unit 70 shirts from rough alignment to fine alignment (S109). For example, in rough alignment, while the examination unit 2 is being moved, the control unit 70 analyzes the anterior segment image Ia captured by the anterior segment imaging optical system 60 in parallel. In a case where an alignment mark projected onto the cornea by the alignment mark projection optical system 50 is detected as a result of the analysis of the anterior segment image Ia, the control unit 70 shirts from rough alignment to fine alignment.

For example, in the fine alignment in the present example, the control unit 70 controls driving of the drive unit 4 on the basis of the alignment mark projected by the alignment mark projection optical system 50, and performs alignment in the XY directions for causing the measurement optical axis of the examination unit 2 to match the cornea center or the pupil center and alignment in the Z direction for adjusting a distance between the examination unit and the cornea of the subject eye to a predetermined working distance.

For example, in the present example, as the alignment in the XY directions, the control unit 70 changes a position of the examination unit 2 such that the measurement optical axis of the examination unit 2 and the cornea center match each other on the basis of the ring mark 51*a* projected by the ring mark projection optical system 51 (alignment in the XY directions). For example, the position of the examination unit 2 in the XY directions is changed such that the center of the ring of the ring mark 51*a* and the measurement optical axis match each other, and thus the cornea center and the measurement optical axis match each other.

For example, in the present example, as the alignment in the Z direction, the control unit 70 detects an alignment state in the working distance direction on the basis of a ratio between an interval of the infinity mark 52*a* projected by the mark projection optical system 52 and a diameter of the ring mark 51*a* projected by the ring mark projection optical system 51, and moves the examination unit 2 on the basis of the detection result. For the working distance alignment technique, for example, the technique disclosed in JPH10-127581A may be used, which is desired to be referred to. An alignment method based on these marks is an example of fine alignment, and a configuration and a method are not limited to this.

Next, when the fine alignment is completed, the control unit 70 automatically issues a trigger signal for starting measurement, and the measurement optical system 20 of the examination unit 2 starts measuring the subject eye. For example, the examination unit 2 measures an eye refractive power of the subject eye (S110).

Next, the control unit 70 controls driving of the drive unit 4 on the basis of a position corresponding to the unmeasured left eye pupil EPL out of the positions of the left and right pupils acquired in S101, and performs rough alignment (S111).

Thereafter, the control unit 70 performs fine alignment in the same manner as for the subject eye that has already been measured (S112), and when the alignment is completed, automatically issues a trigger signal and performs measurement (S113).

(2) In Case where Designated Position is Input for Face Image

Next, an operation in a case where a designated position is input for the face image If will be described, focusing on differences from the operation in a case where the position of the subject eye can be detected normally (in a case where the designated position is not input).

The control unit 70 analyzes the face image If captured by the face imaging unit 3 to start detection of positions of the pupils of the left and right eyes (S101). Here, the subject's mascara, eyelashes, ptosis, or the like may cause a position of the subject eye to be erroneously detected, and as a result, pupil detection using face image analysis will fail (that is, an acquisition error will occur). A case where a position of the subject eye is erroneously detected also includes a case where a position of the subject eye is not detected. In this case, the control unit 70 determines whether pupil detection using face image analysis has succeeded within a predetermined period of time (S103). If a position of the pupil is not acquired within a predetermined period of time (timeout), the control unit 70 determines that pupil detection has failed (acquisition error).

Figure 8:
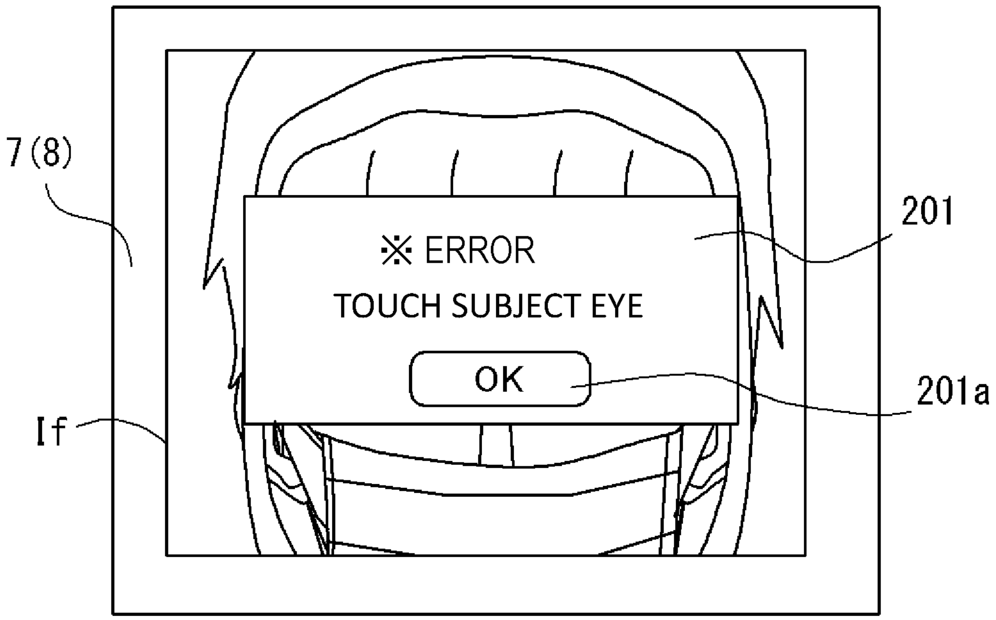
FIG. 8 is a schematic diagram of the display in a case where a position of a subject eye is not detected through the analysis of the face image.

If pupil detection fails (S103: No), the control unit 70 performs error processing (S106). In the present example, for example, as error processing, the control unit 70 displays, on the display 7, that a position of the subject eye (pupil position) is not detected correctly, and notifies the examiner that it is necessary to designate a position corresponding to the subject eye by using the operation unit 8. For example, as illustrated in FIG. 8, the control unit 70 displays a message 201 indicating that the pupil on the face image displayed on the display 7 is touched (refer to FIG. 8). The message 201 is erased by touching an "OK" display 201*a*, and the display 7 shirts to a state in which input is accepted.

In a case where the examiner touches the screen of the display 7 while the face image is displayed on the display 7 and designates a position for the face image (S102), the control unit 70 acquires the position on the face image touched by the examiner as a position of the pupil instead of a position of the pupil detected by using face image analysis in S101, and performs the rough alignment by controlling the drive unit 4 by using the input designated position.

Touching the display 7 is an example of a method of designating a pupil position on the face image, and the present invention is not limited to this. For example, a pupil position on the face image may be designated by using a method such as a mouse or a button.

Figure 9:
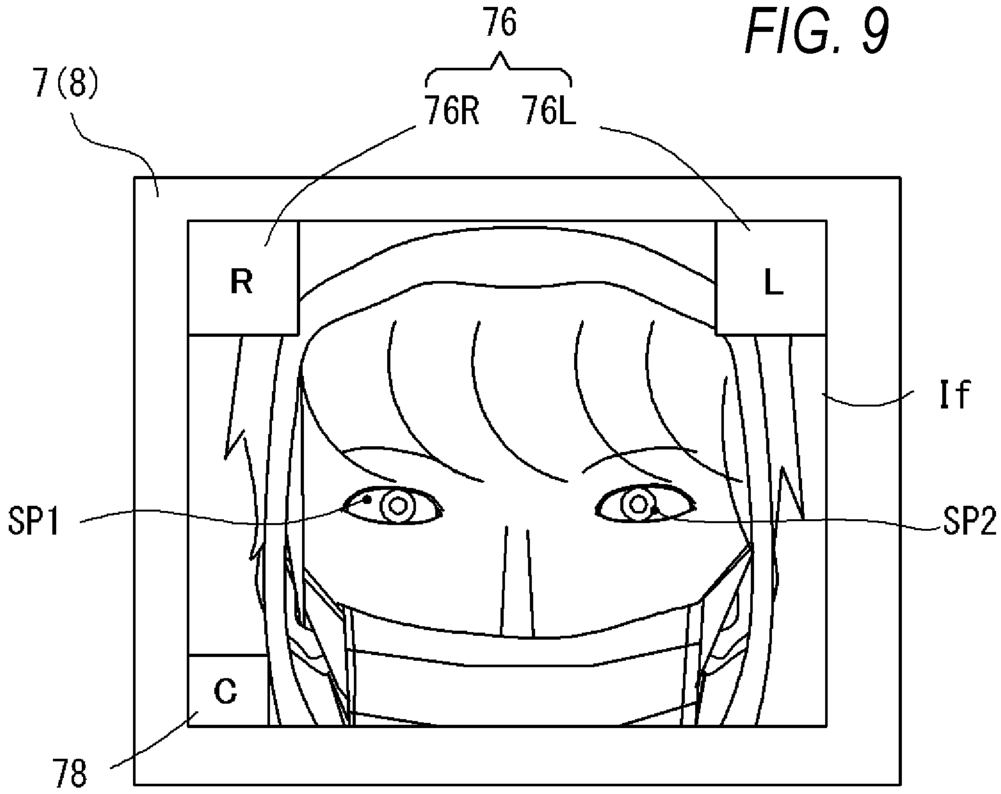
FIG. 9 is a schematic diagram of the display in a case where a position on the face image is input by an examiner.

Here, for example, as illustrated in FIG. 9, two designated positions such as a designated position SP1 corresponding to the right eye of the subject and a designated position SP2 corresponding to the left eye can be input for the face image If, the control unit 70 waits to start rough alignment until the second designated position is input. In a case where the second designated position is not input within a predetermined period of time, the control unit 70 may display a message for prompting the examiner to input the second designated position.

Of course, display of this message is an example of the notification unit, and the present invention is not limited to this, and the examiner may be prompted to perform an input operation for a designated position by using other means such as voice or blinking of light.

The face image If on the display 7 when the examiner inputs a designated position corresponding to the subject eye may be displayed as a moving image or a still image captured by the face imaging unit 3.

For example, in a case where a position on the face image If is designated on a moving image, the control unit 70 may display a still image of the face image If at the time at which the designated position is input on the display 7. For example, the control unit 70 may temporarily switch the display of the display 7 from a moving image to a still image while the examiner is touching the display 7 to input the designated position. Of course, a designated position on a still image may be changeable according to the examiner's input. For example, the control unit 70 may stop the pupil detection process based on the face image while the examiner is changing the designated position on the still image.

In a case where the designated position corresponding to the subject eye is input for the face image If, the control unit 70 acquires coordinates of the designated position, and obtains a direction in which the examination unit 2 is to be moved on the basis of the acquired coordinates (S107), and controls the drive unit 4 to perform rough alignment of the examination unit 2 (S108). A method of performing rough alignment on the basis of input of the designated position will be described below with reference to the flowchart of FIG. 5.

In a case where two positions are designated for the face image displayed on the display 7 within a predetermined period of time, the control unit 70 acquires coordinates of each of the designated positions on the face image If displayed on the display 7 (S201). For example, in the present example, in a case where the examiner touches the positions of the left and right pupils on the face image If displayed on the display 7, coordinates of the positions SP1 and SP2 corresponding to the pupils of the left and right subject eyes are acquired (refer to FIG. 9).

The control unit 70 may control display of the display 7 such that the examiner can ascertain a position where the examiner has touched, and display visually distinguishable marks to be superimposed on the touched positions SP1 and SP2. The control unit 70 may display a left-right display 76 including a right-side display 76R indicating the right eye of the subject on the left side of the face image If and a left-side display 76L indicating the left eye of the subject on the right side of the face image If such that the examiner does not confuse the left and right subject eyes in the face image If displayed on the display 7. The control unit 70 may display a clear button 78 such that the examiner can redo the input in a case where the examiner accidentally touches. For example, in a case where the clear button 78 is pressed, the control unit 70 discards the input position and accepts input from the examiner again. The control unit 70 may store, in the storage unit 74, the face image If when the designated position is input for the face image If and the mark of the input position. In that case, the control unit 70 may call up the image and display the image on the display 7 such that the designated position can be checked.

In a case where the examiner designates identical positions of the left and right subject eyes twice or more, the control unit 70 may acquire the last input position as a designated position. In this case, the control unit 70 may detect that identical positions of the left and right subject eyes have been input, by using the determination unit that will be described later.

Next, the control unit 70 determines positions of the left and right subject eyes respectively corresponding to the two designated positions (S202). For example, the control unit 70 determines the left and right subject eyes on the basis of a positional relationship between the two designated positions. That is, the control unit 70 refers to coordinates on the display 7 for each of the two designated positions and compares the positions in the x direction. According to this, the control unit 70 can obtain a left-right relationship between the two designated positions. For example, the left designated position corresponds to the right subject eye, and the right designated position corresponds to the left subject eye, so that the two designated positions can be associated with the left and right subject eyes. Determination of left and right with respect to two designated positions may be performed on the basis of a positional relationship between the designated positions for the face image If. That is, it is determined assuming that with respect to the face image If, a designated position present in the left region corresponds to the right eye, and a designated position present in the right region corresponds to the left eye. The left region and the right region are, for example, experimentally predetermined regions.

Next, the control unit 70 determines a designated position corresponding to a predetermined eye to be measured first out of the two positions on the basis of the left/right determination results performed in S202, and obtains a direction in which the examination unit 2 is to be moved on the basis of coordinates of the determined position corresponding to the subject eye (S203). As a method of determining a direction in which the examination unit 2 is to be moved for rough alignment, the two-dimensional coordinates (x,y) on the face image, which are positions of the pupils detected through analysis of the face image in S105 described above, may be replaced with the coordinates (x,y) of the designated position that is designated by the examiner.

In the present example, which of the left and right subject eyes is to be measured first is set in advance and stored in the storage unit 74. Instead of a subject eye to be measured first being determined in advance, a subject eye corresponding to a previously designated position out of the two positions designated by the examiner in S201 may be measured first. In this case, the control unit 70 associates the left and right determination results with the left and right measurement results.

Next, the control unit 70 performs rough alignment by controlling the drive unit 4 on the basis of the designated position and moving the examination unit 2 in the obtained direction (S108). Incidentally, in the rough alignment, a position of the jaw rest 11 may be adjusted on the basis of the designated position for the face image If. For example, in a case where the Y-direction position of the subject eye corresponding to the designated position is outside a movement range of the examination unit 2 (optical axis L1) by the drive unit 4, the control unit 70 may control driving of the jaw rest drive unit 12 to move the jaw rest 11 in the Y direction such that a position of the subject eye corresponding to the designated position enters the movement range of the examination unit 2.

Next, similarly to the case where the position of the subject eye is normally detected through the analysis of the face image described above, when the alignment mark projected onto the anterior segment by the alignment mark projection optical system 50 comes to be detected through analysis of the anterior segment image, the control unit 70 shirts from control for performing rough alignment to control for performing fine alignment. The control unit 70 controls the driving of the drive unit 4 to perform fine alignment based on the alignment mark of the anterior segment image (S109). In a case where the fine alignment is completed, the control unit 70 performs measurement on the subject eye (S110).

Thereafter, the control unit 70 performs rough alignment for the unmeasured subject eye out of the left and right subject eyes (S111). In this case, the control unit 70 determines a direction in which the examination unit 2 is to be moved by using the coordinates (x, y) corresponding to the other unmeasured subject eye among the coordinates of the designated positions for the face image If acquired in S107. The control unit 70 performs rough alignment by moving the examination unit 2 in the obtained direction (S111).

Thereafter, the control unit 70 performs fine alignment (S112) and measurement (S113) in the same manner as in the method performed on the subject eye measured first.

According to the above, even in a case where position detection of the subject eye through analysis of the face image is defective, smooth automatic alignment can be performed while reducing the time and effort of the examiner compared with the case where the examiner performs manual alignment.

<One-Eye Examination>

Next, an example of one-eye examination (examination of only one of the left and right subject eyes) will be described. For example, the ophthalmic apparatus 1 includes a subject eye selection switch (subject eye selection means) (not illustrated) for selecting a both-eye examination mode for consecutively examining the right eye and left eye of the subject, a right-eye examination mode for selectively examining only the right eye out of the left and right subject eyes, a left-eye examination mode for examining only the left eye.

Here, in a case where one-eye examination of the right eye or left eye is selected, in the face image displayed on the screen of the display 7, the right eye of the subject is displayed to be located on the left side of the screen, the left eye is displayed to be located on the right side of the screen, and the left and right eyes of the subject are reversed in left-right direction as viewed from the examiner. Therefore, in the one-eye examination, the examiner may mistakenly recognize the left and right subject eyes, and designate a wrong position of the subject eye.

Therefore, the control unit 70 guides the examiner to input a designated position to a selected eye for the face image. For example, the control unit 70 controls the display of the display 7 and performs guidance display such that an eye to be touched by the examiner can be recognized.

Figure 10:
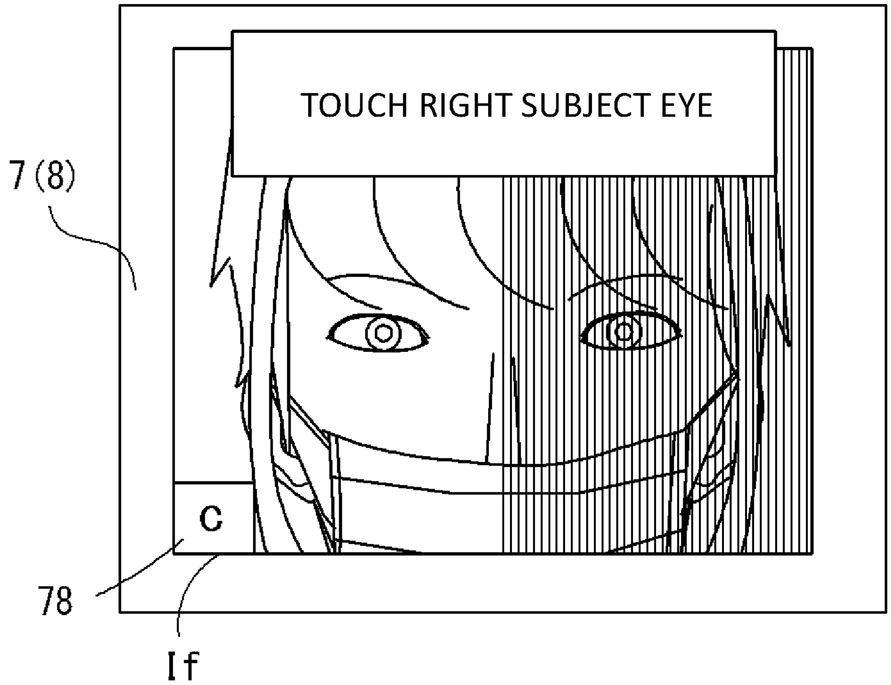
FIG. 10 is a diagram for describing display of the display in a case where the examiner is guided to input a designated position toward an eye selected on the face image.
Figure 11:
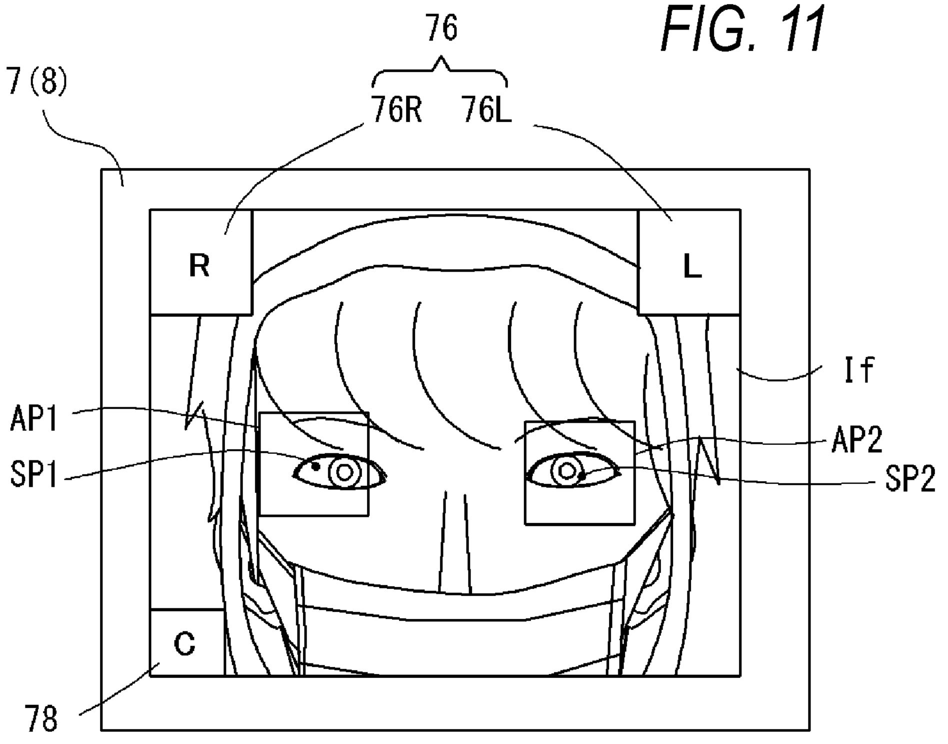
FIG. 11 is a schematic diagram of the display in a case where the position of the subject eye is detected on the basis of the position on the face image input by the examiner.

For example, in a case where the right eye is selected, as illustrated in FIG. 10, the control unit 70 displays a difference between the luminance of the left region from the left-right center of the face image and the luminance of the right region from the left-right center in the face image If displayed on the display 7. With such guidance display, it is possible to guide the examiner to touch a subject eye included in the side with the higher luminance (the eye that is emphasized) out of the left side and the right side of the face image to designate a position.

The guidance display is not limited to the example in FIG. 10. For example, regarding the right-side display 76R and the left-side display 76L in FIG. 9, an eye selected by the subject eye selection switch may be displayed to be distinguishable from the other. For example, the control unit 70 changes a color corresponding to the selected eye to a predetermined color (for example, orange).

MODIFICATION EXAMPLES

In the above-described example, as an example of performing rough alignment using the designated positions (SP1, SP2), when the designated positions (SP1, SP2) are input from the operation unit 8, an example in which driving of the drive unit 4 switches from control based on a detection result of a position of a subject eye detected through analysis of the face image to control based on a designated position has been described, but the present invention is not limited to this. For example, in a case where a designated position is input by the operation unit 8, control may be performed as follows: a pupil position is detected through analysis of the face image within a predetermined region (AP1, AP2) with reference to the designated position (SP1, SP2); and the drive unit 4 is driven on the basis of the pupil positions (EPR, EPL) detected through the analysis in the predetermined region (refer to FIG. 11). This control method is suitably applied in a case where a wrong part is detected as a pupil as a case of defective detection of a position of the pupil through analysis of the face image (the pupil may be erroneously detected due to, for example, shadow of hair or a mask covering the nose and the mouth, a black part of the background outside the face, noise of reflected light due to makeup, moles, eye patches, scars, eyebrows, or eyelashes). This control method is suitably applied even in a case where the examiner touches the display 7 with a finger, and the examiner is not skilled enough to accurately touch and designate a position of the pupil.

In a case where a subject eye is not detected as a result of face image analysis performed within the predetermined region (AP1, AP2), the control unit 70 may perform alignment on the designated position (SP1, SP2). In that case, the control unit 70 may display a message on the display 7 to notify the examiner that a subject eye has not been detected and that alignment is to be performed on the designated position (SP1, SP2).

In order to detect that a wrong part has been detected as a pupil, the control unit 70 may obtain the reliability on the basis of features of the detected part (for example, a difference in contrast with the surroundings and a shape). For example, the reliability is a value for evaluating the features of the detected part. For example, in a case where the reliability is less than a predetermined threshold value, the control unit 70 may determine that a wrong part has been detected as the pupil, and request the examiner to input a designated position.

Figure 12:
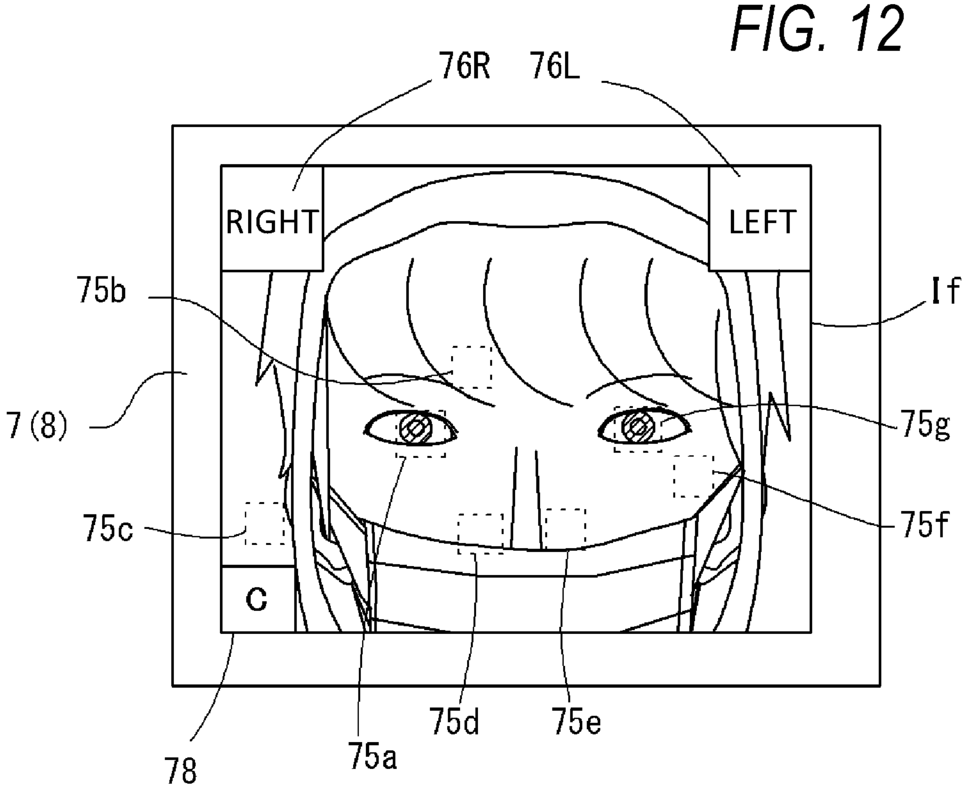
FIG. 12 is a schematic diagram of the display in a case where a plurality of candidate regions detected as pupils on the face image are displayed.

Control for performing rough alignment using the designated position (SP1, SP2) may be performed as follows. That is, for example, in a case where a wrong part is detected as the pupil in position detection of the pupil through analysis of the face image, as illustrated in FIG. 12, a plurality of candidate regions *75a*, *75b*, *75c*, *75d*, *75e*, *75f*, and *75g* detected as the pupil are displayed on the display 7. The examiner checks display of the candidate regions *75a* to *75g* and touches and designates a position of a region to be identified as the pupil among the candidate regions. As a result, the control unit 70 limits the region of the designated position to a detection target of a pupil position, controls the drive unit 4 on the basis of the pupil position detected through analysis, and performs rough alignment.

In the above example, the designated position for the face image is input in a case where detection of a position of the subject eye fails (in a case of acquisition error), but the present invention is not limited to this. For example, if detection of a position of the subject eye based on the face image takes a long time, rough alignment cannot be performed easily, and the examiner waits without operating the ophthalmic apparatus 1. Therefore, the examiner may feel that it takes a long time to transition to fine alignment. In order to favorably perform the automatic alignment even in such a case, when the control unit 70 receives input of a designated position from a touch panel or the like while detecting a position of the subject eye based on the face image, the control unit 70 may perform rough alignment on the basis of the input of the designated position regardless of position detection of the subject eye based on the face image.

In the above embodiment, a case where the examiner designates two pupil positions for the face image If and then rough alignment is performed has been described. However, rough alignment may be performed after one designated position is input. Alternatively, for example, in a case where the second designated position is not input within a predetermined period of time, rough alignment using the first input designated position may be started. The control in that case will be described with reference to the flowcharts of FIGS. 4 and 6.

Figure 6:
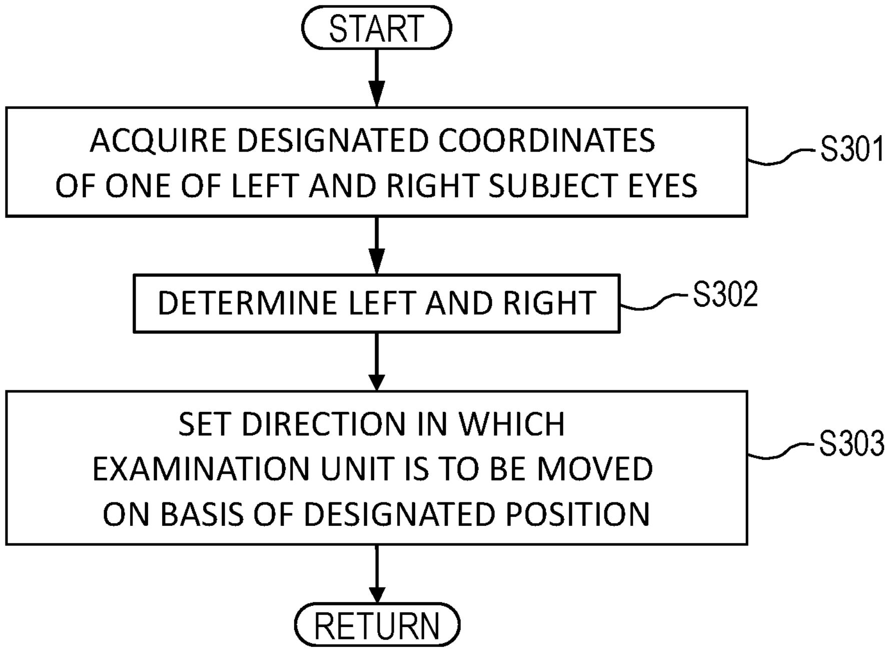
FIG. 6 is a flowchart illustrating an operation of the ophthalmic apparatus in a case where a position of either of left and right subject eyes is input.

In the flowchart in FIG. 4, in a case where there is an input on the display 7 in S102, the control unit 70 acquires the coordinates of the designated position in S107 and uses the result to obtain a direction in which the examination unit 2 is to be moved. The process in S107 in a case where there is one designated position is illustrated in the flowchart of FIG. 6. The control unit 70 receives an input for designating one pupil position for a predetermined period of time, and acquires the coordinates of the designated position (S301). If there is no input within a predetermined period of time, for example, the apparatus times out. In a case where the apparatus times out, for example, the control unit 70 may notify the examiner to touch the face image displayed on the display 7 to input the pupil position.

Next, the control unit 70 determines which of the left and right subject eyes corresponds to the designated position (S302). As an example of a determination method, for example, the control unit 70 may determine that the position of the right subject eye has been designated in a case where the left half of the face image is touched from the left-right central axis of the face image, and determine that the position of the left subject eye is designated in a case where the right half thereof is touched from the left-right central axis of the face image. The left-right center is an example of a criterion for dividing the face image, and may differ depending on configurations of apparatuses.

Next, a direction in which the examination unit 2 is to be moved is obtained on the basis of the designated coordinates (two-dimensional coordinates) (x, y) on the face image (S303), and rough alignment is performed (S108 in FIG. 4). Regarding a method of this rough alignment, the rough alignment may be performed in the same manner as in the above-described case where the positions of both subject eyes are designated and rough alignment is performed on one thereof. That is, rough alignment may be performed by substituting the designated coordinates (x,y) on the face image in the alignment control based on the coordinates (x,y) obtained through analysis of the face image.

Next, the control unit 70 performs fine alignment in the same manner as described above (S109), and measures the aligned subject eye (S110).

Next, the control unit 70 performs rough alignment on the unmeasured subject eye (S111). In a case where there is one input position of the subject eye, on the basis of the left/right determination result in S302, measurement of the subject eye of which the designated position has been input is completed, then the subject eye of which a designated position is not input is identified, and rough alignment is performed by moving the examination unit 2 in the direction of the subject eye.

Since the left and right subject eyes are at substantially the same height in the Y direction, the control unit 70 does not move the examination unit 2 in the Y direction, and controls the drive unit 4 to move the examination unit 2 in the X direction. In this case, the control unit 70 moves the examination unit 2 in the direction in which the other eye is present on the basis of the result of left/right determination. The positions of the left and right subject eyes are substantially even on the left and right with respect to the center of the subject's face. Therefore, an amount of movement in which the examination unit 2 is to be moved in the X direction may be obtained on the basis of an amount of movement of the examination unit 2 with respect to a reference position (center position) of the base 5 when measuring one subject eye. For example, an amount of movement of the examination unit 2 with respect to the reference position (center position) of the base 5 in the X direction may be obtained from drive data of the drive unit 4 in the X direction. Since a position of the examination unit 2 in the Z direction with respect to the subject eye can be considered to be substantially the same for the left and right subject eyes, a Z-direction position of the examination unit 2 at the time of measurement of one subject eye may be used. With this configuration, the control unit 70 performs rough alignment on the other subject eye, analyzes the anterior segment image Ia acquired by the anterior segment imaging optical system 60, and performs, when the alignment mark is detected, fine alignment on the basis of the detection result. After the fine alignment is completed, the control unit 70 automatically issues a trigger signal to execute measurement using the measurement optical system 20. In a case where measurement results for both eyes are obtained, the control unit 70 outputs measurement results for each of the left and right eyes corresponding to the left/right determination result in S302.

According to the above, even in a case where the examiner inputs the position of only one of the left and right subject eyes, favorable alignment can be performed.

In the present example, for example, the face image If displayed on the display 7 may be enlarged and reduced. For example, the examiner may be able to enlarge or reduce the image by pinching on the touch panel. For example, in this case, the examiner may be able to designate a position of the subject eye in the Z direction on the basis of an amount of enlargement/reduction of the face image.

The ophthalmic apparatus 1 may have a configuration of using machine learning to increase the accuracy with which the control unit 70 detects the subject eye from the face image If from the next time on, on the basis of the information on a position designated on the face image If. In that case, the control unit 70 acquires parameters such as coordinates of the position designated on the face image and a contrast difference between the designated position and its surroundings as success factors. For example, on the basis of the obtained success factors, the control unit 70 increases the detection accuracy of the subject eye through face image analysis from the next time onward.

What is claimed is:

1. An ophthalmic apparatus comprising:

an examination unit configured to examine a subject eye;

a drive unit configured to three-dimensionally move the examination unit relative to the subject eye;

a first imaging unit configured to capture a face image including left and right subject eyes;

a second imaging unit configured to capture an anterior segment image of the subject eye;

a display unit configured to display the face image captured by the first imaging unit;

at least one processor and memory having stored therein programmed instructions configured to be executed by the processor and when executed by the processor perform operations, comprising:

a first acquisition that detects positions of the left and right subject eyes by analyzing the face image, and acquire the positions of the left and right subject eyes identified through the detection as a detected positions;

a second acquisition that acquires the position of the subject eye identified based on a designated position from an input operation of designating coordinates on the face image displayed on the display unit, in which the face image is displayed on the display unit before the first acquisition completes the detection; and a position acquisition of collectively acquiring positions of the left and right subject eyes, in which the positions are the detected positions in a case where the first acquisition detects the detected positions, and the positions are the designated positions by the input operation for each subject eye, regardless of whether the first acquisition detects the detected positions, in a case where the second acquisition acquires the positions of the left and right subject eyes even after the first acquisition starts the detection;

a first drive control of controlling the drive unit, such that the subject eye is positioned within an imaging range of the second imaging unit, based on the acquired position of the subject eye; and a second drive control of controlling the drive unit based on the anterior segment image after the first drive control, to adjust a relative position of the examination unit with respect to the subject eye, wherein:

when a left eye and a right eye are consecutively examined, the programmed instructions when executed by the processor carries out collective acquisition of respective positions of the left eye and the right eye in the position acquisition of the adjustment process performed for one subject eye to be examined first out of the left eye and the right eye, when the positions of the left eye and the right eye are collectively acquired in the position acquisition, the ophthalmic apparatus is configured to allow input operation for each eye to be requested, and when the left eye and the right eye are consecutively examined, the programmed instructions when executed by the processor carries out the first drive control for a secondly-examined eye based on a position of the secondly-examined eye acquired by the second acquisition, regardless of whether the first acquisition acquires the position of the secondly-examined eye, in the case where the second acquisition already acquires the positions of the left and right subject eyes.

2. The ophthalmic apparatus according to claim 1, wherein the second acquisition detects a position of the subject eye based on an analysis of a part of the face image using coordinates designated through the input operation in the face image as a reference, and is further configured to acquire the position of the subject eye identified through the detection as the designated position.

3. The ophthalmic apparatus according to claim 1, wherein the programmed instructions when executed by the processor:

controls a notification unit to perform a notification for requesting an examiner to perform an input operation for the designated position when an acquisition error of the detected position occurs in the adjustment process using the detected position.

4. The ophthalmic apparatus according to claim 1, wherein the programmed instructions when executed by the processor:

determines that the designated position is for the left subject eye or the right subject eye, based on whether the designated position is present in a right eye region or a left eye region in the face image captured by the first imaging unit when the single designated position is designated through the input operation, performs the first drive control based on the designated position input through the input operation and then shift to the second drive control;

determines left or right for a relative movement of the examination unit with respect to the subject eye based on a determination result from the determination unit in order to examine an unexamined subject eye after an examination of one of the left and right subject eyes is completed; and controls the drive unit, such that the examination unit approaches the unexamined subject eye, based on the determined result of left or right, and shift to the second drive control.

5. A non-transitory computer-readable storage medium storing a control program for an ophthalmic apparatus including a drive unit configured to three-dimensionally move an examination unit, which examines a subject eye, relative to the subject eye, a first imaging unit configured to capture a face image including left and right subject eyes, a second imaging unit configured to capture an anterior segment image of the subject eye, and a display unit configured to display the face image captured by the first imaging unit, the control program comprising instructions which, when executed by a controller of the ophthalmic apparatus, cause the ophthalmic apparatus to perform:

a first acquisition step of detecting positions of the left and right subject eyes by analyzing the face image, and acquiring the positions of the left and right subject eyes identified through the detection as detected positions;

a second acquisition step of acquiring the position of the subject eye identified based on the input operation as a designated position of designating coordinates on the face image displayed on the display unit, in which the face image is displayed on the display unit before the detection in the first acquisition step completes; and a control step of performing an adjustment process with respect to one of the left and right subject eyes, the adjustment process including:

a position acquisition of collectively acquiring positions of the left and right subject eyes, in which the positions are the detected positions in a case where the first acquisition step detects the detected positions, and the positions are the designated positions by the input operation for each subject eye, regardless of whether the first acquisition unit detects the detected positions, in a case where the designated positions of the left and the right subject eyes are acquired in the second acquisition step even after the detection in the first acquisition step starts;

a first drive control of controlling the drive unit, such that the subject eye is positioned within an imaging range of the second imaging unit, based on the acquired position of the subject eye; and a second drive control of controlling the drive unit based on the anterior segment image after the first drive control, to adjusting a relative position of the examination unit with respect to the subject eye, wherein:

when a left eye and a right eye are consecutively examined, the controller programming when executed carries out collective acquisition of respective positions of the left eye and the right eye in the position acquisition of the adjustment process performed for one subject eye to be examined first out of the left eye and the right eye, when the positions of the left eye and the right eye are collectively acquired in the position acquisition, the ophthalmic apparatus is configured to allow input operation for each eye to be requested, and when the left eye and the right eye are consecutively examined, the ophthalmic apparatus performs the first drive control for a secondly-examined eye based on a position of the secondly-examined eye acquired in the second acquisition step, regardless of whether the position of the secondly-examined eye is acquired in the first acquisition step, in the case where the positions of the left and right subject eyes are already acquired in the second acquisition step.

* * * * *